(12) United States Patent
Vogt

(10) Patent No.: US 9,408,944 B2
(45) Date of Patent: Aug. 9, 2016

(54) PASTE-LIKE BONE CEMENT

(71) Applicant: Heraeus Medical GmbH, Wehrheim (DE)

(72) Inventor: Sebastian Vogt, Erfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 0 days.

(21) Appl. No.: 13/949,511

(22) Filed: Jul. 24, 2013

(65) Prior Publication Data

US 2014/0031451 A1 Jan. 30, 2014

(30) Foreign Application Priority Data

Jul. 25, 2012 (DE) .......................... 10 2012 014 702

(51) Int. Cl.
*A61L 24/04* (2006.01)
*A61L 27/46* (2006.01)
*A61L 24/00* (2006.01)

(52) U.S. Cl.
CPC ............ *A61L 24/043* (2013.01); *A61L 24/0073* (2013.01); *A61L 24/0084* (2013.01); *A61L 24/0089* (2013.01); *A61L 27/46* (2013.01); *A61L 2430/02* (2013.01)

(58) Field of Classification Search
CPC ............ A61L 24/0073; A61L 24/0084; A61L 24/043; A61L 27/446; A61L 27/46; A61L 2400/06; A61L 2430/02; C08L 33/12
USPC .................................................. 523/115, 116
See application file for complete search history.

(56) References Cited

U.S. PATENT DOCUMENTS

| | | | | |
|---|---|---|---|---|
| 3,873,475 | A * | 3/1975 | Pechacek | C08K 7/22 427/142 |
| 4,015,945 | A | 4/1977 | Frankel et al. | |
| 5,264,215 | A * | 11/1993 | Nakabayashi et al. | 424/423 |
| 5,968,999 | A | 10/1999 | Ramp et al. | |
| 7,223,808 | B2 | 5/2007 | Müller et al. | |
| 8,153,704 | B2 * | 4/2012 | Lavergne et al. | 523/117 |
| 8,598,251 | B2 | 12/2013 | Vogt et al. | |
| 9,144,626 | B2 | 9/2015 | Vogt et al. | |
| 2004/0129650 | A1 | 7/2004 | Beruto et al. | |
| 2004/0175409 | A1 | 9/2004 | Müller et al. | |
| 2005/0256220 | A1 | 11/2005 | Lavergne et al. | |
| 2008/0248086 | A1 * | 10/2008 | Asgari | 424/426 |
| 2008/0269909 | A1 | 10/2008 | Vogt et al. | |
| 2009/0105366 | A1 | 4/2009 | Vogt et al. | |
| 2009/0221730 | A1 * | 9/2009 | Kowalski et al. | 523/116 |
| 2010/0086620 | A1 | 4/2010 | Meyer et al. | |
| 2010/0272649 | A1 * | 10/2010 | Nies et al. | 424/9.4 |
| 2011/0095045 | A1 * | 4/2011 | Speck | B44D 3/12 222/1 |
| 2011/0313078 | A1 | 12/2011 | Vogt et al. | |
| 2013/0210960 | A1 * | 8/2013 | Lee et al. | 523/116 |
| 2015/0051305 | A1 | 2/2015 | Sattig et al. | |

FOREIGN PATENT DOCUMENTS

| | | |
|---|---|---|
| DE | 102007050763 A1 | 4/2009 |
| DE | 102007052116 A1 | 4/2009 |
| DE | 102007050762 B3 | 5/2009 |
| DE | 102010055759 A1 | 7/2011 |
| DE | 10 2010 024653 A1 | 12/2011 |
| EP | 0674888 A1 | 10/1995 |
| EP | 2 359 872 A2 | 8/2011 |
| JP | H 04-189363 A | 7/1992 |
| JP | 002002085545 A | 3/2002 |
| JP | 2003181270 A | 7/2003 |
| JP | 2004 528950 A | 9/2004 |
| JP | 2008264556 A | 11/2008 |
| JP | 2009 101159 A | 5/2009 |
| JP | 2012 005829 A | 1/2012 |
| JP | 2012 085857 A | 5/2012 |
| WO | 2007007065 A2 | 1/2007 |
| WO | 2007/025633 A2 | 3/2007 |
| WO | 2011/038905 A2 | 4/2011 |
| WO | 2012018612 A2 | 2/2012 |

OTHER PUBLICATIONS

German Office Action for corresponding German Application No. DE10 2012 014 702.3 dated Mar. 22, 2013.
Charnley, John; "Anchorage of the Femoral Head Prosthesis to the Shaft of the Femur"; The Journal of Bone and Joint Surgery; Feb. 1960; pp. 28-30; Manchester, England.
Australian Examination Report for corresponding Australian Patent Application No. 2013207604 dated May 27, 2014.
Notice of Reasons for Rejection issued in corresponding application JP 2013-142689 transmitted Sep. 30, 2014.
Japanese Office Action, with English Language Translation for corresponding Japanese Patent Application No. 2013-142689 dated Aug. 18, 2015.
European Search Report dated Jan. 20, 2016.

* cited by examiner

*Primary Examiner* — Tae H Yoon
(74) *Attorney, Agent, or Firm* — Norris McLaughlin & Marcus, P.A.

(57) ABSTRACT

A paste contains at least one monomer for radical polymerization, at least one polymer that is soluble in said at least one monomer for radical polymerization, and at least one filling agent that is poorly soluble or insoluble in said at least one monomer for radical polymerization. The filling agent is a particulate inorganic calcium salt comprising the following properties: at least 90% by weight of the particulate inorganic calcium salt have a particle size of less than 63 μm, as determined by means of sieve analysis; and the solubility in water of the particulate inorganic calcium salt at 20° C. is less than 8.5 g per liter. A kit and the paste is usable for mechanical fixation of articular endoprostheses, for covering skull defects, for filling bone cavities, for femuroplasty, for vertebroplasty, for kyphoplasty, for the manufacture of spacers or for the production of carrier materials for local antibiotics therapy, as well as a form body.

7 Claims, No Drawings

PASTE-LIKE BONE CEMENT

The present invention relates to a paste, a kit, the use of a paste or of a paste produced from a kit for mechanical fixation of articular endoprostheses, for covering skull defects, for filling bone cavities, for femuroplasty, for vertebroplasty, for kyphoplasty, for the manufacture of spacers or for the production of carrier materials for local antibiotics therapy, as well as a form body.

Conventional polymethylmethacrylate bone cements (PMMA bone cements) have been known for decades and are based on the ground-breaking work of Sir Charnley (Charnley, J.: "*Anchorage of the femoral head prosthesis of the shaft of the femur*"; J. Bone Joint Surg. 42 (1960) 28-30). The basic structure of PMMA bone cements has remained the same ever since. PMMA bone cements consist of a liquid monomer component and a powder component. The monomer component generally contains (i) the monomer, methylmethacrylate, and (ii) an activator (e.g. N,N-dimethyl-p-toluidine) dissolved therein. The powder component comprises (i) one or more polymers that are made by polymerisation, preferably by suspension polymerisation, based on methyl-methacrylate and co-monomers, such as styrene, methylacrylate or similar monomers, (ii) a radio-opaquer, and (iii) an initiator, (e.g. dibenzoylperoxide). Mixing the powder component and the monomer component, the polymers of the powder component in the methylmethacrylate swell which generates a dough that can be shaped plastically. Simultaneously, the activator, N,N-dimethyl-p-toluidine, reacts with dibenzoylperoxide which disintegrates and forms radicals in the process. The radicals thus formed trigger the radical polymerisation of the methylmethacrylate. Upon advancing polymerisation of the methylmethacrylate, the viscosity of the cement dough increases until the cement dough solidifies and thus is cured.

The essential disadvantage of the previous PMMA bone cements for the medical user is that the user needs to mix the liquid monomer component and the powder component in a mixing system or in crucibles right before applying the cement. Mixing errors can easily occur in the process and adversely affect the quality of the cement. Moreover, the components must be mixed rapidly. In this context, it is important to mix all of the cement powder and monomer component without forming lumps and prevent the introduction of air bubbles during the mixing process. Unlike manual mixing, the use of vacuum mixing systems prevents the formation of air bubbles in the cement dough to a large extent. Examples of mixing systems are disclosed in patent specifications U.S. Pat. No. 4,015,945, EP-A-0 674 888, and JP-A-2003181270. However, vacuum mixing systems necessitate an additional vacuum pump and are therefore relatively expensive. Moreover, depending on the type of cement concerned, a certain waiting time is required after mixing the monomer component and the powder component until the cement dough is tack-free and can be applied. Because of the large variety of errors that can occur while mixing conventional PMMA bone cements, appropriately trained personnel is required for this purpose. The corresponding training is associated with considerable expenses. Moreover, mixing of the liquid monomer component and the powder component is associated with exposure of the user to monomer vapours and particles released from the powder-like cement.

Pasty polymethylmethacrylate bone cements containing a methacrylate monomer for radical polymerisation, a polymer that is soluble in said methacrylate monomer, and a particulate polymer that is insoluble in said methacrylate monomer have been described as an alternative to the conventional powder-liquid polymethylmethacrylate bone cements in unexamined German patent applications DE-A-10 2007 052 116, DE-A-10 2007 050 762, and DE-A-10 2007 050 763. Paste-like polymethylmethacrylate bone cements of this type can be present as one-component systems (in this case, the paste contains all components required for curing, in particular an activatable radical initiator, e.g. a photoinitiator or a photoinitiator system) or as two-component systems (in this case, the system comprises two pre-mixed pastes that are stable on storage and one of which comprises a radical polymerisation initiator and the other comprises a polymerisation activator). Referring to two-component systems, a distinction is made between a "symmetrical system" (in this case both pastes contain a particulate polymer that is insoluble in the methacrylate monomer) and "non-symmetrical systems" (in this case, only one of the two pastes contains a particulate polymer that is insoluble in the methacrylate monomer).

As a result of the selected composition, the bone cement produced from the pastes described above possesses sufficiently high viscosity and cohesion in order to withstand the pressure from bleeding until it is fully cured. Owing to the advancing polymerisation, the paste is cured while the methacrylate monomers are consumed.

Aside from at least one monomer for radical polymerisation and at least one polymer dissolved therein, the pasty polymethylmethacrylate bone cements disclosed in DE-A-10 2007 052 116, DE-A-10 2007050 762, and DE-A-10 2007 050 763 contain polymer particles that are insoluble in said monomer. Said insoluble polymer particles are a filling agent. Said filling agent has a significant influence on the viscosity of the cement pastes. The polymer particles are essential for the processing properties to ensure that the cement pastes show as little restoring motion as possible during the application phase of the shaping process. This allows the cement pastes to be moulded into any shape during the processing phase such as is generally known for conventional polymethylmethacrylate bone cements that are based on the mixing of polymer powder and monomer liquid.

The production of cross-linked polymer particles that are insoluble in methacrylate monomers is relatively laborious and therefore expensive. For this reason, it is desirable to identify an alternative, inexpensive particulate material which, after admixture into mixtures of methacrylate monomers and polymers dissolved therein, yields pastes that show only minimal elastic resilience after shaping much like cross-linked polymer particles.

However, one problem is that the cross-linked polymer particles used thus far also contributed to the mechanical stability of the cured pasty cements. It is therefore important to identify an alternative filling agent which not only ensures that the pastes have the requisite processing properties, but also does not adversely affect the mechanical parameters of the cured cements such that the mechanical stability requirements of ISO 5833 are met.

The present invention was based on the object to overcome the disadvantages of prior art bone cement systems that are based on pastes, in particular with regard to the two-component systems described above.

In particular, the present invention was based on the object to provide a bone cement paste, in particular a bone cement paste based on a two-component system, which can be produced from less expensive starting materials than bone cement pastes known according to the prior art, but still features the same processing properties as the pastes according to the prior art.

A contribution to meeting the objects stated above is made by a paste containing at least one monomer for radical polymerisation, at least one polymer that is soluble in said at least one monomer for radical polymerisation, and at least one filling agent that is poorly soluble or insoluble in said at least one monomer for radical polymerisation, whereby the filling agent is a particulate inorganic calcium salt comprising the following properties i) and ii):

i) at least 90% by weight, particularly preferably at least 95% by weight, and most preferably 100% by weight of the particulate inorganic calcium salt have a particle size of less than 63 µm, particularly preferably of less than 20 µm, and most preferably of less than 10 µm as determined by means of sieve analysis;

ii) the solubility in water of the particulate inorganic calcium salt at 20° C. is less than 8.5 g per liter, particularly preferably less than 5 g per liter, and most preferably less than 3 g per liter.

The invention is based on finding that bone cement pastes that can be formed and shaped well can be produced through the use of particulate inorganic calcium salts from the sieve fraction smaller than 63 µm (in accordance with DIN 66165-1/-2), which was a surprise considering the previously known pasty polymethylmethacrylate bone cements. The surprise being that the hitherto customary cross-linked polymer particles that are insoluble in methacrylate monomers can be replaced fully or partly by particulate inorganic calcium salts. Inorganic calcium salts are markedly less expensive than cross-linked polymer particles and can therefore be used to economic advantage in the production of pasty polymethylmethacrylate bone cements. Surprisingly, calcium carbonate from the sieve fraction smaller than 63 µm, in particular, was found to be particularly well-suited as a filling agent.

The hardness of inorganic calcium salts, such as, for example, calcium carbonate, is relatively low. Accordingly, calcium carbonate (calcite) is characterised by a hardness of 2 according to Mohs. Due to the hardness being low, it was expected that the incorporation of particulate inorganic calcium salts into polymethylmethacrylate pastes would render the cured pastes incapable of meeting the 4-point flexural strength, flexural modulus, and compressive strength requirements of ISO 5833. It was therefore quite surprising that it was feasible to produce cement pastes that met the mechanical requirements of ISO 5833 after curing despite the use of particulate inorganic calcium salts instead of cross-linked polymer particles.

As a matter of principle, the paste according to the invention can be a one-component system of the type described above or can be obtained through mixing the two pastes of a two-component system of the type described above.

The paste according to the invention contains, as a component, at least one monomer for radical polymerisation, whereby this is preferably a methacrylate monomer, in particular a methacrylate monomer that is liquid at a temperature of 25° C. and a pressure of 1,013 hPa.

Preferably, the monomer for radical polymerisation is not a bisphenol A-derived methacrylic acid ester.

Preferably, the methacrylate monomer is a methacrylic acid ester. Preferably, the methacrylic acid ester is a monofunctional methacrylic acid ester. Preferably, said substance is hydrophobic. The use of hydrophobic monofunctional methacrylic acid esters allows later increases in bone cement volume due to the uptake of water and thus damage to the bone to be prevented. According to a preferred embodiment, the monofunctional methacrylic acid ester is hydrophobic if it contains no further polar groups aside from the ester group. The monofunctional hydrophobic methacrylic acid ester preferably comprises no carboxyl groups, hydroxyl groups, amide groups, sulfonic acid groups, sulfate groups, phosphate groups or phosphonate groups.

The esters preferably are alkyl esters. According to the invention, cycloalkyl esters are also included in alkyl esters. According to a preferred embodiment, the alkyl esters are esters of methacrylic acid and alcohols comprising 1 to 20 carbon atoms, more preferably 1 to 10 carbon atoms, even more preferably 1 to 6 carbon atoms, and particularly preferably 1 to 4 carbon atoms. The alcohols can be substituted or non-substituted and preferably are non-substituted. Moreover, the alcohols can be saturated or unsaturated and preferably are saturated.

The monomer for radical polymerisation used according to the invention preferably has a molar mass of less than 1,000 g/mol. This also comprises monomers for radical polymerisation that are components of a mixture of monomers, whereby at least one of the monomers for radical polymerisation of the mixture of monomers has a defined structure with a molar mass of less than 1,000 g/mol.

The monomer for radical polymerisation is preferably characterised in that an aqueous solution of the monomer for radical polymerisation has a pH in the range of 5 to 9, preferably in the range of 5.5 to 8.5, even more preferably in the range of 6 to 8, and particularly preferably in the range of 6.5 to 7.5.

According to a particularly preferred embodiment, the methacrylate monomer is a methacrylic acid methylester, methacrylic acid ethylester or a mixture of said two monomers.

Preferably, the paste according to the invention contains an amount of the monomer for radical polymerisation in a range of 15 to 85% by weight, more preferably 20 to 70% by weight, even more preferably 25 to 60% by weight, and particularly preferably 25 to 50% by weight, each relative to the total weight of the paste according to the invention.

The paste according to the invention contains, as further component, at least one polymer that is soluble in said at least one monomer for radical polymerisation. According to the invention, a polymer is soluble in the polymerisable monomer, if at least 10 g/l, preferably at least 25 g/l, more preferably at least 50 g/l, and particularly preferably at least 100 g/l of the polymer dissolve in said polymerisable monomer. The polymer that is soluble in the polymerisable monomer can be a homopolymer or a copolymer. Said soluble polymer preferably is a polymer with a mean (by weight) molar mass of at least 150,000 g/mol. The soluble polymer can, for example, be a polymer or copolymer of a methacrylic acid ester. According to a particularly preferred embodiment, the at least one soluble polymer is selected from the group consisting of polymethacrylic acid methylester (PMMA), polymethacrylic acid ethylester (PMAE), polymethacrylic acid propylester (PMAP), polymethacrylic acid isopropylester, poly(methylmethacrylate-co-methylacrylate), poly(styrene-co-methylmethacrylate), and a mixture of at least two of said polymers.

The amount of the polymer that is soluble in said monomer for radical polymerisation that is present in the paste usually is in a range of 1 to 85% by weight, relative to the total weight of the paste according to the invention.

Moreover, the paste according to the invention contains at least one particulate inorganic calcium salt that is poorly soluble or insoluble in the at least one monomer for radical polymerisation and has the above-defined properties i) and ii) as a filling agent.

According to a preferred refinement of the paste according to the invention, the particulate inorganic calcium salt is selected from the group consisting of calcium carbonate, dolomite, calcium sulfate dihydrate, α-tricalcium phosphate, β-tricalcium phosphate, hydroxyapatite, octacalcium phosphate, amorphous calcium phosphate, fluoroapatite, chloroapatite, carbonate apatite, and a mixture of at least two of these substances. Particularly preferred amongst these are particulate inorganic calcium salt is selected from the group consisting of calcium carbonate, dolomite, calcium sulfate dihydrate, β-tricalcium phosphate, hydroxyapatite, and a mixture of at least two of these substances, whereby calcium carbonate is most preferred as particulate inorganic calcium salt.

The amount of the particulate inorganic calcium salt that is present in the paste according to the invention usually is in a range of 0.5 to 25% by weight, particularly preferably from 1 to 20% by weight, and most preferably in a range of 5 to 15% by weight, each relative to the total weight of the paste. Aside from the particulate inorganic calcium salt described above, the paste according to the invention can also contain certain amounts of another filling agent, if applicable, for example the cross-linked polymer particles that are known according to the prior art, whereby the weight ratio of particulate inorganic calcium salt to cross-linked polymer particles in this case preferably is at least 1:15 (i.e. at least approx. 6% by weight particulate inorganic calcium salt relative to the total amount of filling agent), particularly preferably is at least 1:1 (i.e. at least 50% by weight particulate inorganic calcium salt relative to the total amount of filling agent).

Preferably, the paste according to the invention is tack-free in accordance with ISO 5833 no later than 15 minutes after being produced.

Moreover, the paste according to the invention can contain at least one polymerisation initiator (which preferably is soluble in the monomer for radical polymerisation), at least one polymerisation accelerator (which preferably is soluble in the monomer for radical polymerisation), at least one polymerisation co-accelerator, if applicable, or at least one polymerisation initiator, at least one polymerisation accelerator, and, if applicable, at least one polymerisation co-accelerator.

In the case of a one-component system, the polymerisation initiator preferably is an activatable polymerisation initiator, e.g. a photoinitiator that is dissolved or suspended in the paste or a photoinitiator system that is dissolved or suspended in the paste. It is feasible just as well to provide an initiator or initiators where it/they are temporarily in contact with the paste, for example in a container part, a dosing facility or a transport cannula. Moreover, in a one-component system, the paste according to the invention can also contain an electrically conductive radio-opaquer aside from the activatable polymerisation initiator. Particles made of cobalt, iron, NdFeB, SmCo, cobalt-chromium steel, zirconium, hafnium, titanium, titanium-aluminium-silicon alloys, and titanium-niobium alloys having a particle size of 0.5-500 μm are particularly well-suited in this context. It is feasible to induce eddy currents in said electrically conductive radio-opaquer through alternating magnetic fields with a frequency in the range of 500 Hz to 50 kHz which cause the radio-opaquer to heat up. Due to heat transmission, the initiator is heated as well and induced to thermally disintegrate.

In the case of a paste according to the invention that was obtained through combining two pastes of a two-component system, said paste preferably contains at least one polymerisation initiator (that was contained in the one paste of the two-component system) and at least one polymerisation accelerator (that was contained in the other paste of the two-component system).

Conceivable as polymerisation initiator are, in particular, peroxides and barbituric acid derivatives, whereby preferably at least 1 g/l, more preferably at least 3 g/l, even more preferably at least 5 g/l, and particularly preferably at least 10 g/l of the peroxides and barbituric acid derivatives can dissolve(s) in the polymerisable monomer at a temperature of 25° C.

According to the invention, a peroxide is understood to mean compounds that contain at least one peroxo group (—O—O—). The peroxide preferably comprises no free acid groups. The peroxide can be an inorganic peroxide or an organic peroxide, such as, for example, a toxicologically acceptable hydroperoxide. According to a particularly preferred embodiment, the peroxide is selected from the group consisting of cumene-hydroperoxide, 1,1,3,3-tetramethylbutyl-hydroperoxide, t-butyl-hydroperoxide, t-amyl-hydroperoxide, di-isopropylbenzen-mono-hydroperoxide, and a mixture of at least two of these substances.

The barbituric acid derivative preferably is a barbituric acid derivative selected from the group consisting of 1-mono-substituted barbiturates, 5-mono-substituted barbiturates, 1,5-di-substituted barbiturates, and 1,3,5-tri-substituted barbiturates. According to a particular refinement of the paste according to the invention, the barbituric acid derivative is selected from the group consisting of 1,5-di-substituted barbiturates and 1,3,5-tri-substituted barbiturates.

There is no limitation with regard to the type of substituents on the barbituric acid. The substituents can, for example, be aliphatic or aromatic substituents. In this context, alkyl, cycloalkyl, allyl or aryl substituents can be preferred. The substituents can also include hetero atoms. In particular, the substituents can be thiol substituents. Accordingly, 1,5-disubstituted thiobarbiturates or 1,3,5-trisubstituted thiobarbiturates can be preferred. According to a preferred embodiment, the substituents each have a length of 1 to 10 carbon atoms, more preferably a length of 1 to 8 carbon atoms, and particularly preferably a length in the range of 2 to 7 carbon atoms. According to the invention, barbiturates bearing one substituent each at position 1 and position 5 or a substituent at positions 1, 3, and 5 are preferred. According to another preferred embodiment, the barbituric acid derivative is a 1,5-disubstituted barbiturate or a 1,3,5-trisubstituted barbiturate. According to a particularly preferred embodiment, the barbituric acid derivative is selected from the group consisting of 1-cyclohexyl-5-ethyl-barbituric acid, 1-phenyl-5-ethyl-barbituric acid, and 1,3,5-trimethyl-barbituric acid.

Heavy metal compounds selected from the group consisting of heavy metal salts and heavy metal complexes are preferred as polymerisation accelerator.

Heavy metal compounds that are preferred according to the invention are selected from the group consisting of copper(II) hydroxide, copper(II) methacrylate, copper(II) acetylacetonate, copper(II)-2-ethyl-hexanoate, cobalt(II) hydroxide, cobalt(II)-2-ethyl-hexanoate, basic copper(II) carbonate, iron(II)-2-ethyl-hexanoate, iron(III)-2-ethyl-hexanoate, and a mixture of at least two of these substances.

According to another refinement of the paste according to the invention, the polymerisation accelerator is selected from the group consisting of N,N-dimethyl-p-toluidine, N,N-bis-hydroxyethyl-p-toluidine, N,N-dimethyl-aniline, trioctylmethylammoniumchloride, tetrabutylammoniumchloride, lithium chloride, saccharin, 1,8-diazabicyclo[5.4.0]undec-7-ene, and 1,5-diazabicyclo(4.3.0)non-5-ene, phthalimide, maleimide, succinimide, pyromellitic acid diimide, and a mixture of at least two of these substances.

Another advantageous refinement of the invention consists of the use, as polymerisation accelerator, of combinations of heavy metal salts and at least one member of the group consisting of N,N-dimethyl-p-toluidine, N,N-bis-hydroxyethyl-p-toluidine, N,N-dimethyl-aniline, trioctylmethylammoniumchloride, tetrabutylammoniumchloride, lithium chloride, saccharin, 1,8-diazabicyclo[5.4.0]undec-7-ene, and 1,5-diazabicyclo(4.3.0)non-5-ene, phthalimide, maleimide, succinimide, and pyromellitic acid diimide. Combinations of two and combinations of three different polymerisation accelerators in this context are included in the scope of the invention.

An advantageous refinement of the invention consists of the paste according to the invention containing at least one polymerisation co-accelerator, if applicable, whereby tertiary amines and amidines are preferred as polymerisation co-accelerators, and whereby N,N-dimethyl-p-toluidine, N,N-bis-hydroxyethyl-p-toluidine, N,N-dimethyl-aniline, 1,8-diazabicyclo[5.4.0-]undec-7-ene, and 1,5-diazabicyclo(4.3.0)-non-5-ene are particularly preferred as co-accelerators.

The paste according to the invention can contain a (total) amount of up to 10% by weight, relative to the total weight of the paste according to the invention, of the polymerisation initiator, polymerisation accelerator, polymerisation co-accelerator or polymerisation accelerator and polymerisation co-accelerator.

The paste according to the invention can contain further ingredients aside from the components specified above.

According to a preferred embodiment of the paste according to the invention, said paste can contain at least one radio-opaquer. The radio-opaquer can be a common radio-opaquer in this field. Suitable radio-opaquers can be soluble or insoluble in the monomer for radical polymerisation. The radio-opaquer is preferably selected from the group consisting of metal oxides (such as, for example, zirconium oxide), barium sulfate, toxicologically acceptable heavy metal particles (such as, for example, tantalum), ferrite, magnetite (supramagnetic magnetite also, if applicable), and biocompatible calcium salts. Said radio-opaquers preferably have a mean particle diameter in the range of 10 nm to 500 µm. Moreover, conceivable radio-opaquers also include esters of 3,5-bis(acetamido)-2,4,6-triiodobenzoic acid, gadolinium compounds, such as gadolinium chelate involving the esters of 1,4,7,10-tetraazacyclododecan-1,4,7,10-tetraacetic acid (DOTA). The concentration of radiopaquer, in particular the concentration of zirconium dioxide, that is present in the paste according to the invention can, for example, be in a range of 3 to 30% by weight.

According to a further preferred embodiment, the paste according to the invention can contain at least one colourant. The colourant can be a common colourant in this field and preferably can be a food colourant. Moreover, the colourant can be soluble or insoluble in the at least one monomer for radical polymerisation. According to a particularly preferred embodiment, the colourant is selected from the group consisting of E101, E104, E132, E141 (chlorophyllin), E142, riboflavin, and lissamine green. According to the invention, the term, colourant, shall also include colour varnishes, such as, for example, colour varnish green, the aluminium salt of a mixture of E104 and E132.

According to a further preferred embodiment, the paste according to the invention can contain at least one pharmaceutical agent. The at least one pharmaceutical agent can be present in the paste according to the invention in dissolved or suspended form. The pharmaceutical agent can preferably be selected from the group consisting of antibiotics, antiphlogistic agents, steroids, hormones, growth factors, bisphosphonates, cytostatic agents, and gene vectors. According to a particularly preferred embodiment, the at least one pharmaceutical agent is an antibiotic. Preferably, the at least one antibiotic is selected from the group consisting of aminoglycoside antibiotics, glycopeptide antibiotics, lincosamide antibiotics, gyrase inhibitors, carbapenems, cyclic lipopeptides, glycylcyclines, oxazolidones, and polypeptide antibiotics. According to a particularly preferred embodiment, the at least one antibiotic is a member selected from the group consisting of gentamicin, tobramycin, amikacin, vancomycin, teicoplanin, dalbavancin, lincosamine, clindamycin, moxifloxacin, levofloxacin, ofloxacin, ciprofloxacin, doripenem, meropenem, tigecycline, linezolide, eperezolide, ramoplanin, metronidazole, timidazole, omidazole, and colistin, as well as salts and esters thereof. Accordingly, the at least one antibiotic can be selected from the group consisting of gentamicin sulfate, gentamicin hydrochloride, amikacin sulfate, amikacin hydrochloride, tobramycin sulfate, tobramycin hydrochloride, clindamycin hydrochloride, lincosamine hydrochloride, and moxifloxacin. The at least one antiphlogistic agent is preferably selected from the group consisting of non-steroidal antiphlogistic agents and glucocorticoids. According to a particularly preferred embodiment, the at least one antiphlogistic agent is selected from the group consisting of acetylsalicylic acid, ibuprofen, diclofenac, ketoprofen, dexamethasone, prednisone, hydrocortisone, hydrocortisone acetate, and fluticasone. The at least one hormone is preferably selected from the group consisting of serotonin, somatotropin, testosterone, and estrogen. Preferably, the at least one growth factor is selected from the group consisting of fibroblast growth factor (FGF), transforming growth factor (TGF), platelet derived growth factor (PDGF), epidermal growth factor (EGF), vascular endothelial growth factor (VEGF), insulin-like growth factors (IGF), hepatocyte growth factor (HGF), bone morphogenetic protein (BMP), interleukin-1B, interleukin 8, and nerve growth factor. The at least one cytostatic agent is preferably selected from the group consisting of alkylating agents, platinum analogues, intercalating agents, mitosis inhibitors, taxanes, topoisomerase inhibitors, and antimetabolites. The at least one bisphosphonate is preferably selected from the group consisting of zoledronate and aledronate.

According to a further preferred embodiment, the paste according to the invention can contain at least one biocompatible elastomer. Preferably, the biocompatible elastomer is particulate. Preferably, the biocompatible elastomer is soluble in the at least one monomer for radical polymerisation. The use of butadiene as biocompatible elastomer has proven to be particularly well-suited.

According to a further preferred embodiment, the paste according to the invention can contain at least one monomer having adsorption groups. The adsorption group can, for example, be an amide group. Accordingly, the monomer with adsorption group can, for example, be methacrylic acid amide. Using at least one monomer with adsorption groups would allow the binding of the bone cement to articular endoprostheses to be influenced in a targeted manner.

According to a further preferred embodiment, the paste according to the invention can contain at least one stabiliser. The stabiliser should be suitable to prevent spontaneous polymerisation of the monomers for radical polymerisation that are contained in the paste. Moreover, the stabiliser should not undergo interfering interactions with the other ingredients contained in the paste according to the invention. Stabilisers of said type are known according to the prior art. According to a preferred embodiment, the stabiliser is 2,6-di-tert-butyl-4-methylphenol and/or 2,6-di-tert-butyl-phenol.

A kit comprising a paste A and a paste B also makes a contribution to a solution meeting the object specified above, whereby
(a) paste A contains
   (a1) at least one monomer for radical polymerisation;
   (a2) at least one polymer that is soluble in (a1); and
   (a3) at least one polymerisation initiator;

(b) paste B contains
  (b1) at least one monomer for radical polymerisation;
  (b2) at least one polymer that is soluble in (b1); and
  (b3) at least one polymerisation accelerator;
and whereby at least one of the pastes A and B contains, as component (a4) or (b4), respectively, at least one filling agent that is poorly soluble or insoluble in (a1) or (b1), respectively, whereby the filling agent is a particulate inorganic calcium salt that comprises the following properties i) and ii):
i) at least 90% by weight, particularly preferably at least 95% by weight, and most preferably 100% by weight of the particulate inorganic calcium salt have a particle size of less than 63 µm, particularly preferably of less than 20 µm, and most preferably of less than 10 µm as determined by means of sieve analysis;
ii) the solubility in water of the particulate inorganic calcium salt at 20° C. is less than 8.5 g per liter, particularly preferably less than 5 g per liter, and most preferably less than 3 g per liter.

According to the invention, a kit shall be understood to be a system made up of at least two components. Although reference to two components (i.e. paste A and paste B) is made in the following, the kit can just as well contain more than two components, for example three, four, five or more than five components, according to need. The individual components preferably are provided to be packaged separate from each other such that the ingredients of the one kit component do not contact the ingredients of another kit component. Accordingly, it is feasible, for example, to package the respective kit components separate from each other and to store them together in a reservoir container.

Preferably, the kit is designed as a kit for producing bone cement comprising a first container and a second container, whereby the first container comprises paste A and the second container comprises paste B, whereby at least one of the containers can be opened to allow for paste A and paste B to be mixed after the opening, and a mixing unit for the mixing of pastes A and B.

The components described above in the context of the paste according to the invention as preferred monomer for radical polymerisation, as polymer that is soluble in said monomer, as polymerisation initiator, as polymerisation accelerator, and as particulate inorganic calcium salt are preferred as monomer (a1) and/or (b1) for radical polymerisation, as polymer that is soluble in (a1) and/or (b1), as polymerisation initiator (a3), as polymerisation accelerator (b3), and as particulate inorganic calcium salt (a4) and/or (b4), respectively.

Preferably, paste A and paste B contain an amount of the at least one monomer for radical polymerisation (a1) and/or (b1) in a range of 15 to 85% by weight, more preferably 20 to 70% by weight, even more preferably 25 to 60% by weight, and particularly preferably 25 to 50% by weight, each relative to the total weight of paste A and/or paste B.

Preferably, paste A contains an amount of the polymerisation initiator (a3) in a range of 0.01 to 10% by weight, more preferably in a range of 0.01 to 8% by weight, and even more preferably in a range of 0.01 to 5% by weight, each relative to the total weight of paste A.

Provided the polymerisation accelerator (b3) is a heavy metal compound selected from the group consisting of heavy metal salts and heavy metal complexes, in particular is a heavy metal compound selected from the group consisting of copper(II) hydroxide, copper(II) methacrylate, copper(II) acetylacetonate, copper(II)-2-ethyl-hexanoate, cobalt(II) hydroxide, cobalt(II)-2-ethyl-hexanoate, basic copper(II) carbonate, iron(II)-2-ethyl-hexanoate, iron(III)-2-ethyl-hexanoate, and a mixture of at least two of these substances, paste B preferably contains an amount of said polymerisation accelerator (b3) in a range of 0.0005 to 0.5% by weight, relative to the total weight of paste B.

Provided the polymerisation accelerator (b3) is a compound selected from the group consisting of N,N-dimethyl-p-toluidine, N,N-bis-hydroxyethyl-p-toluidine, N,N-dimethyl-aniline, trioctylmethylammoniumchloride, tetrabutylammoniumchloride, lithium chloride, saccharin, 1,8-diazabicyclo[5.4.0]undec-7-ene, 1,5-diazabicyclo(4.3.0) non-5-ene, phthalimide, maleimide, succinimide, pyromellitic acid diimide, and a mixture of at least two of these substances, paste B preferably contains an amount of said polymerisation accelerator (b3) in a range of 0.1 to 10% by weight, relative to the total weight of paste B.

Specifically, paste A can further contain as component (a5) the polymerisation co-accelerator described above, which preferably is a compound selected from the group consisting of N,N-dimethyl-p-toluidine, N,N-bis-hydroxyethyl-p-toluidine, N,N-dimethyl-aniline, 1,8-diazabicyclo[5.4.0]undec-7-ene, 1,5-diazabicyclo(4.3.0)non-5-ene, and a mixture of at least two of these substances. It is preferred in this context for paste A to contain an amount of the at least one polymerisation co-accelerator (a5) in a range of 0.1 to 10% by weight, relative to the total weight of paste A.

Provided one of the pastes of the kit according to the invention contains the poorly soluble or insoluble filling agent and the other paste contains no poorly soluble or insoluble filling agent at all or contains a negligible amount of poorly soluble or insoluble filling agent as compared to the amount present in the other paste, the kit is called "asymmetrical". In contrast, a so-called "symmetrical" kit has approximately comparable amounts of the poorly soluble or insoluble filling agent present in both pastes.

Moreover, pastes A and/or B can contain further additives aside from the components described above, such as radioopaquers, colourants, pharmaceutical agents, biocompatible elastomers, monomers having adhesion groups or stabilisers, whereby the components described above, in the context of the paste according to the invention, as preferred radioopaquers, colourants, pharmaceutical agents, biocompatible elastomers, monomers having adhesion groups, and stabilisers are preferred here as well.

According to a first particular refinement of the kit according to the invention, the kit is an "asymmetrical" kit. It is preferred in this context that paste A contains 20 to 70% by weight, particularly preferably 25 to 60% by weight, even more preferably 30 to 55% by weight, and most preferably 34 to 47% by weight, each relative to the total weight of paste A, of the filling agent (a4) that is insoluble in (a1), and paste B contains less than 5% by weight, particularly preferably less than 1% by weight, even more preferably less than 0.1% by weight, and yet more preferably less than 0.01% by weight, each relative to the total weight of paste B, of the filling agent (b4) that is insoluble in (b1), whereby it is most preferred that paste B contains no filling agent (b4) that is insoluble in (b1) at all.

Moreover, in the context of said first particular refinement of the kit according to the invention, it is preferred for paste A to contain an amount of the polymer (a2) that is soluble in (a1) in a range of 1 to 25% by weight, particularly preferably in a range of 2 to 20% by weight, even more preferably in a range of 2 to 18% by weight, and most preferably in a range of 3 to 16% by weight, each relative to the total weight of paste A, and for paste B to contain an amount of a polymer (b2) that is soluble in (b1) in a range of 25 to 85% by weight, particularly preferably in a range of 35 to 85% by weight, even more preferably in a range of 35 to 80% by weight, and most preferably in a range of 35 to 75% by weight, each relative to the total weight of paste B.

Moreover, it is preferred in the context of said first particular refinement of the kit according to the invention that the weight ratio of filling agent (b4) that is insoluble in (b1) to the at least one polymer (b2) that is soluble in (b1) is no more than 0.2, more preferably no more than 0.15, even more preferably no more than 0.1, yet more preferably no more than 0.05, particularly preferably no more than 0.02, and even more particularly preferably is equal to 0.

According to a second particular refinement of the kit according to the invention, the kit is a "symmetrical" kit. It is preferred in this context that paste A contains 15 to 85% by weight, particularly preferably 15 to 80% by weight, and even more preferably 20 to 75% by weight, each relative to the total weight of paste A, of the filling agent (a4) that is insoluble in (a1), and paste B contains 15 to 85% by weight, particularly preferably 15 to 80% by weight, and even more preferably 20 to 75% by weight, each relative to the total weight of paste B, of the filling agent (b4) that is insoluble in (b1).

Moreover, in the context of said second particular refinement of the kit according to the invention, it is preferred that paste A contains an amount of a polymer (a2) that is soluble in (a1) in a range of 5 to 50% by weight, particularly preferably in a range of 10 to 40% by weight, and even more preferably in a range of 20 to 30% by weight, each relative to the total weight of paste A, and/or paste B contains an amount of a polymer (b2) that is soluble in (b1) in a range of 5 to 50% by weight, particularly preferably in a range of 10 to 40% by weight, and even more preferably in a range of 20 to 30% by weight, each relative to the total weight of paste B.

According to the invention, the purpose of the paste and/or kit according to the invention containing at least pastes A and B is the production of bone cement.

Referring to the kit, for this purpose, the at least two pastes A and B are mixed with each other, upon which another paste, paste C, is obtained. The mixing ratio preferably is 0.5 to 1.5 parts by weight of paste A and 0.5 to 1.5 parts by weight of paste B. According to a particularly preferred embodiment, the fraction of paste A is 30 to 70% by weight and the fraction of paste B is 30 to 70% by weight, each relative to the total weight of pastes A and B, respectively. Mixing can be effected with common mixing devices, for example a static mixer or a dynamic mixer.

After mixing the pastes of the kit, paste C which is ultimately obtained (and corresponds to the paste according to the invention specified above) is tack-free in accordance with the ISO 5833 standard no later than after 15 minutes.

The bone cement generated from paste C by curing attains high strength approximately six to eight minutes after mixing the pastes contained in the kit.

According to a preferred embodiment, paste C and/or the kit according to the invention can be used for mechanical fixation of articular endoprostheses, for covering skull defects, for filling bone cavities, for femuroplasty, for vertebroplasty, for kyphoplasty, for the manufacture of spacers, and for the production of carrier materials for local antibiotics therapy.

In this context, the term, "spacer", shall be understood to mean implants that can be used temporarily as spacer in the scope of the two-step exchange of prostheses in septic revision surgeries.

Carrier materials for local antibiotics therapy can be provided as spheres or sphere-like bodies or as bean-shaped bodies. Besides, it is also feasible to produce rod-shaped or disc-shaped carrier materials that receive the bone cement made from the paste according to the invention and/or the kit according to the invention. Moreover, the carrier materials can also be threaded onto absorbable or non-absorbable suture material in a bead-like manner.

The uses according to the invention of bone cement described above are known from the literature and have been described therein on numerous occasions.

A contribution to meeting the objects specified above is also made by a form body that is obtainable through polymerisation of a paste that is obtainable through mixing paste A and paste B of the kit according to the invention or through polymerisation of a paste according to the invention. Form bodies according to the scope of the present invention can be any three-dimensional bodies, in particular the "spacers" described above.

The invention shall be illustrated through the examples described in the following, though without limiting the scope of the invention.

EXEMPLARY EMBODIMENTS

Pastes A of examples A1-8 were produced by simply mixing the components. The pastes thus formed were then stored over night at room temperature.

| | Paste A | | | | | | | | | |
|---|---|---|---|---|---|---|---|---|---|---|
| | Compositions of pastes A | | | | | | | | | |
| Example no. | CH [mg] | BH [g] | DM [g] | EG [g] | MA [g] | MMA [g] | PL [g] | CA [g] | $ZrO_2$ [g] | Rod [mg] |
| A1 | 50 | 1.40 | 0.60 | 0.1 | 0.4 | 1.70 | 13.0 | 7.0 | 4.8 | 20 |
| A2 | 50 | 1.40 | 0.60 | 0.1 | 0.4 | 1.70 | 13.0 | 9.0 | 4.8 | 20 |
| A3 | 50 | 1.40 | 0.60 | 0.1 | 0.4 | 1.70 | 13.0 | 11.0 | 4.8 | 20 |
| A4 | 50 | 1.40 | 0.60 | 0.1 | 0.4 | 1.70 | 13.0 | 13.0 | 4.8 | 20 |
| A5 | 50 | 1.40 | 0.60 | 0.1 | 0.4 | 1.70 | 13.0 | 14.0 | 4.8 | 20 |
| A6 | 50 | 1.40 | 0.60 | 0.1 | 0.4 | 1.70 | 13.0 | 16.0 | 4.8 | 20 |

-continued

Paste A

Compositions of pastes A

| Example no. | CH [mg] | BH [g] | DM [g] | EG [g] | MA [g] | MMA [g] | PL [g] | CA [g] | ZrO$_2$ [g] | Rod [mg] |
|---|---|---|---|---|---|---|---|---|---|---|
| A7 | 50 | 1.40 | 0.60 | 0.1 | 0.4 | 1.70 | 13.0 | 14.0 | 4.8 | 20 |
| A8 | 50 | 1.40 | 0.60 | 0.1 | 0.4 | 1.70 | 13.0 | 16.0 | 4.8 | 20 |

CH: Cumene hydroperoxide
BH: N,N-Bis-(2-hydroxyethyl)-p-toluidine
DM: N,N-Dimethyl-p-toluidine
EG: Ethylene glycol dimethacrylate
MA: Methacrylamide
MMA: Methylmethacrylate
PL: linear poly(methylmethacrylate-co-methylacrylate) MW <500,000 g/mol
CA: Calcium carbonate (sieve fraction smaller than 63 μm)
ZrO$_2$: Zirconium dioxide
Rod: 2,6-Di-t-butyl-4-methyl-phenol Pastes B of examples B1-8 also were produced by simply mixing the components. The pastes thus formed were then stored over night at room temperature.

Paste B

Compositions of pastes B

| Example no. | SAC [g] | CuOct [mg] | MMA [g] | PL [g] | HM [g] | GS [g] | Rod [mg] |
|---|---|---|---|---|---|---|---|
| B1 | 1.00 | 55 | 21.20 | 17.50 | — | — | 15 |
| B2 | 1.00 | 55 | 21.20 | 17.50 | — | — | 15 |
| B3 | 1.00 | 55 | 21.20 | 17.50 | — | — | 15 |
| B4 | 1.00 | 55 | 21.20 | 17.50 | — | — | 15 |
| B5 | 1.00 | 40 | 21.20 | 17.50 | 0.17 | — | 15 |
| B6 | 1.00 | 45 | 21.20 | 17.50 | 0.17 | — | 15 |
| B7 | 1.00 | 40 | 21.20 | 17.50 | 0.17 | 1.26 | 15 |
| B8 | 1.00 | 45 | 21.20 | 17.50 | 0.17 | 1.26 | 15 |

SAC: Saccharine
CuOct: Copper(II)-2-ethylhexanoate
MMA: Methylmethacrylate
PL: linear poly(methylmethacrylate-co-methylacrylate) MW <500,000 g/mol
HM: Methacrylic acid 2-hydroxyethylester
Rod: 2,6-Di-t-butyl-4-methyl-phenol
GS: Gentamicin sulfate (activity coefficient AK = 621)

Pastes A and B of examples A1-8 and B1-8 were mixed with each other at a weight ratio of 1:1. This produced pastes C that were tack-free right away and had a similar processing phase as conventional high viscosity polymethylmethacrylate bone cements. The processing phase lasted for 4-6 minutes.

The mixed pastes C produced from pastes A and B of examples 1-8 (weight ratio of paste A to paste B of 1:1) were used to produce strip-shaped test bodies with dimensions of (75 mm×10 mm×3.3 mm) for the bending strength and flexural modulus tests and cylindrical test bodies (diameter 6 mm, height 12 mm) were used for the test of compressive strength. The test bodies were then stored for 24 hours on air at 23±1° C. Then the 4-point flexural strength, flexural modulus, and the compressive strength of the test bodies were determined using a Zwick universal testing device.

| Pastes C | Compositions of Pastes C | 4-point flexural strength [MPa] | Flexural modulus [MPa] | Compressive strength [MPa] |
|---|---|---|---|---|
| C1 | A1 + B1 | 63.6 ± 2.1 | 2777 ± 42 | 109.0 ± 3.3 |
| C2 | A2 + B2 | 67.2 ± 1.0 | 2796 ± 40 | 110.2 ± 5.8 |
| C3 | A3 + B3 | 62.7 ± 2.3 | 2713 ± 91 | 101.2 ± 3.2 |
| C4 | A4 + B4 | 60.0 ± 1.7 | 2583 ± 157 | 104.5 ± 3.7 |
| C5 | A5 + B5 | 57.5 ± 2.8 | 2667 ± 105 | 96.2 ± 3.5 |
| C6 | A6 + B6 | 54.9 ± 1.8 | 2523 ± 67 | 91.2 ± 3.5 |
| C7 | A7 + B7 | 57.5 ± 1.5 | 2567 ± 115 | 95.1 ± 1.9 |
| C8 | A8 + B8 | 54.0 ± 2.2 | 2400 ± 137 | 91.1 ± 2.4 |

ISO 5833 defines the following parameters: 4-point flexural strength of at least 50 MPa, flexural modulus of at least 1,800 MPa, and compressive strength of at least 70 MPa. The results of the 4-point flexural strength, flexural modulus, and compressive strength tests on cured pastes C1-8 show that the mechanical stability requirements of ISO 5833 are met.

In addition, pastes were produced using barium sulfate instead of zirconium dioxide. Said pastes had a similar curing behaviour as the pastes C1-8 produced from pastes A1-8 and B1-8.

Moreover, additional pastes B were produced analogous to paste B8 except that each had 1.0 g vancomycin hydrochloride, clindamycin hydrochloride, daptomycin, and octenidine dihydrochloride added. After mixing these pastes B with paste A1 at a weight ratio of 1:1, the mixed pastes C showed similar curing behaviour as the combination of paste A8 and paste B8 at a weight ratio of 1:1.

Furthermore, pastes A were produced analogous to example A1, but using t-butyl-hydroperoxid, t-amyl-hydroperoxide, and dicumyl-peroxide instead of cumene-hydroperoxide. After mixing these pastes A with paste B1 at a weight ratio of 1:1, the mixed pastes showed similar behaviour as the combination of pastes A1 and paste B1.

The invention claimed is:
1. A paste containing at least one monomer for radical polymerisation, at least one soluble polymer that is soluble in said at least one monomer for radical polymerisation, at least one filling agent that is poorly soluble or insoluble in said at least one monomer for radical polymerisation and at least one polymerisation initiator selected from the group of substances consisting of cumene-hydroperoxide, 1,1,3,3-tetramethylbutyl-hydroperoxide, t-butyl-hydroperoxide, t-amyl-hydroperoxide, di-isopropylbenzen-mono-hydroperoxide, and a mixture of at least two of these substances thereof, wherein the at least one filling agent comprises a particulate inorganic calcium salt having the following properties i) and ii):

i) at least 90% by weight of the particulate inorganic calcium salt have a particle size of less than 63 μm, as determined by means of sieve analysis; and ii) the solubility in water of the particulate inorganic calcium salt at 20° C. is less than 8.5 g per liter, wherein the particulate inorganic calcium salt is calcium carbonate present in an amount of 5 to 15% by weight to the total weight of the paste and the amount of particulate inorganic calcium salt is at least 50% by weight relative to the total amount of the at least one filling agent, and further wherein the at least one soluble polymer is selected from the group of soluble polymers consisting of poly(methacrylic acid methylester), poly(methacrylic acid ethylester), poly(methylmethacrylic acid propylester), poly(methacrylic acid isopropylester), poly(methylmethacrylate-co-methylacrylate), poly(styrene-co-methylmethacrylate), and a mixture of at least two of said soluble polymers.

2. The paste according to claim 1, wherein the filling agent comprises the properties i) and ii):

i) at least 90% by weight of the particulate inorganic calcium salt have a particle size of less than 20 μm, as determined by means of sieve analysis; and ii) the solubility in water of the particulate inorganic calcium salt at 20° C. is less than 5 g per liter.

3. The paste according to claim 1, wherein the paste contains, in addition, at least one polymerisation accelerator, and, if applicable, at least one polymerisation co-accelerator.

4. The paste according to claim 1, wherein the paste is tack-free in accordance with ISO 5833 no later than 15 minutes after being produced.

5. A paste containing at least one monomer for radical polymerisation, at least one soluble polymer that is soluble in said at least one monomer for radical polymerisation, at least one filling agent that is poorly soluble or insoluble in said at least one monomer for radical polymerisation and at least one polymerisation initiator selected from the group of substances consisting of cumene-hydroperoxide, 1,1,3,3-tetramethylbutyl-hydroperoxide, t-butyl-hydroperoxide, t-amyl-hydroperoxide, di-isopropylbenzen-mono-hydroperoxide, and a mixture of at least two of these substances thereof, wherein the at least one filling agent comprises a particulate inorganic calcium salt having the following properties i) and ii):

i) at least 90% by weight of the particulate inorganic calcium salt have a particle size of less than 63 μm, as determined by means of sieve analysis; and ii) the solubility in water of the particulate inorganic calcium salt at 20° C. is less than 8.5 g per liter, and wherein the particulate inorganic calcium salt is calcium carbonate or a mixture of calcium carbonate and at least one additional substance and is present in an amount of 5 to 15% by weight to the total weight of the paste and the amount of particulate inorganic calcium salt is at least 50% by weight relative to the total amount of the at least one filling agent, and wherein the at least one additional substance is selected from the group of substances consisting of dolomite, calcium sulfate dihydrate, α-tricalcium phosphate, β-tricalcium phosphate, hydroxyapatite, octacalcium phosphate, amorphous calcium phosphate, fluoroapatite, chloroapatite, carbonate apatite, and a mixture of at least two of these substances thereof.

6. The paste according to claim 5, wherein the at least one additional substance is selected from the group of substances consisting of dolomite, calcium sulfate dihydrate, β-tricalcium phosphate, hydroxyapatite, and a mixture of at least two of these substances thereof.

7. A paste containing at least one monomer for radical polymerisation, at least one soluble polymer that is soluble in said at least one monomer for radical polymerisation, at least one filling agent that is poorly soluble or insoluble in said at least one monomer for radical polymerisation and at least one polymerisation initiator selected from the group of substances consisting of cumene-hydroperoxide, 1,1,3,3-tetramethylbutyl-hydroperoxide, t-butyl-hydroperoxide, t-amyl-hydroperoxide, di-isopropylbenzen-mono-hydroperoxide, and a mixture of at least two of these substances thereof, wherein the at least one filling agent comprises a particulate inorganic calcium salt having the following properties i) and ii):

i) at least 90% by weight of the particulate inorganic calcium salt have a particle size of less than 63 μm, as determined by means of sieve analysis; and ii) the solubility in water of the particulate inorganic calcium salt at 20° C. is less than 8.5 g per liter, wherein the particulate inorganic calcium salt is calcium carbonate present in an amount of 5 to 15% by weight to the total weight of the paste and the amount of particulate inorganic calcium salt is at least 50% by weight relative to the total amount of the at least one filling agent, and further wherein the monomer for radical polymerisation is a methacrylic acid ester.

* * * * *